United States Patent [19]

Werner

[11] Patent Number: 5,292,329
[45] Date of Patent: Mar. 8, 1994

[54] RETRACTABLE SURGICAL KNIFE

[76] Inventor: Richard S. Werner, 2920 W. 38th St., Minneapolis, Minn. 55410

[21] Appl. No.: 986,139

[22] Filed: Dec. 4, 1992

[51] Int. Cl.$^5$ ............................................. A61B 17/32
[52] U.S. Cl. .................................. 606/167; 606/170; 30/162
[58] Field of Search .................. 30/1, 51, 151, 155, 30/159, 160, 162, 161, 272.1, 286, 346; 401/102, 103; 606/167, 170, 172, 181, 182, 171

[56] References Cited

U.S. PATENT DOCUMENTS

| | | |
|---|---|---|
| 2,446,044 | 7/1948 | Davis ................................. 401/103 |
| 2,905,146 | 9/1959 | Johmann ........................... 401/103 |
| 3,144,005 | 8/1964 | Johmann ........................... 401/103 |
| 3,657,812 | 4/1972 | Lee . | 
| 3,906,626 | 9/1975 | Riuli ..................................... 30/320 |
| 5,071,426 | 12/1991 | Dolgin et al. . |
| 5,116,351 | 5/1992 | Frassetti . |
| 5,139,507 | 8/1992 | Dolgin et al. . |
| 5,141,517 | 8/1992 | Shutt . |

Primary Examiner—C. Fred Rosenbaum
Assistant Examiner—Noelle Kent Gring
Attorney, Agent, or Firm—Merchant, Gould, Smith, Edell, Welter & Schmidt

[57] ABSTRACT

A retractable "ball-pen" like tool/scalpel, provided with a latch mechanism, is automatically retracted when not in use by pushing the latch mechanism and is extended when in use by pushing a tool/blade support member of the tool/scalpel. An enlarged section of the latch mechanism is matched and engaged with an enlarged slot portion of the tool/blade support member when the tool/blade support member is pushed to an operative position wherein a tool/blade is exposed from a sheath member. The enlarged section of the latch mechanism is pushed transversely and disengaged with the enlarged slot portion of the tool/blade support member, the tool/blade support member is forced back to an inoperative position wherein the tool/scalpel is retracted into the sheath member.

20 Claims, 3 Drawing Sheets

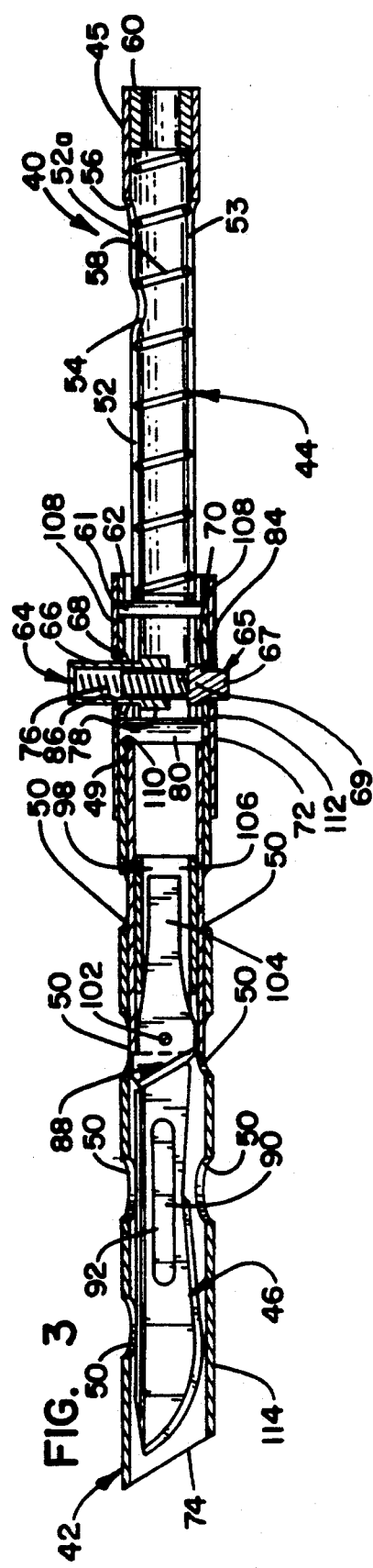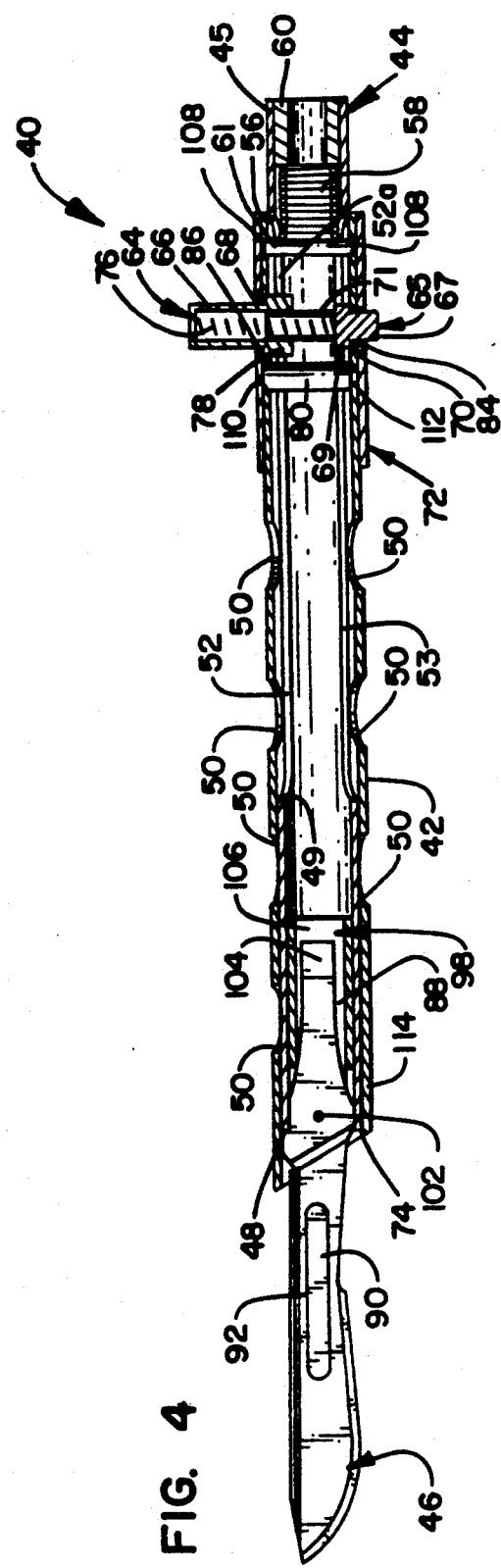

RETRACTABLE SURGICAL KNIFE

FIELD OF THE INVENTION

The present invention relates generally to retractable scalpels and similar devices which have a tool/blade movable between an exposed operative position and a covered nonoperative position. In one embodiment, the invention relates to a protective retractable scalpel in which the blade is extended against the force of a spring to expose a cutting surface, and upon completion of the activity, the cutting surface of the blade is quickly and automatically retracted into a sheath.

BACKGROUND OF THE INVENTION

Scalpels are a class of knives used in the surgical environment for incising, stabbing, shaving, and curetting of human and animal tissue. Conventional scalpels used for this purpose have a stationary blade. The blade is always exposed thereby creating a hazard of inadvertent puncture to an operating team member and to any other person who may come in contact with an instrument. The primary hazard of puncture is the possible transmission of an infectious agent, such as the AIDS virus. It has long been a desire of the medical profession to provide a protective scalpel which completely and absolutely encircles and protects the blade during non-use.

In some emergency situations, a surgeon must work quickly and hand instruments back and forth to assistants. It is dangerous sometimes because the sharp scalpels can accidentally cut or jab the personnel's hands during the operation. Certain fatal infections can be transferred to individuals through small cuts.

Presently existing protective scalpels have removable guards to prevent contact with the blade during non-use. However, with the rapidity in which surgery is conducted, this imposes a degree of inconvenience which would be burdensome. Other conventional protective scalpels include examples in which a blade sheath pivots or extends and retracts upon a given force applied to a handle of the scalpel. These scalpels do not provide absolute security of the blade such as the present invention where the blade is completely encased in a sheath.

Prior art tool retraction/latch mechanisms have the disadvantage of exposed screws, springs, fasteners, gears, links, and the like which, upon certain conditions, could loosen and fall into a wound or cavity.

Another disadvantage of many protective scalpels is the encroachment of a portion of the scalpel blade. This interfaces with normal use of the scalpel, as entire length of the blade is typically used.

Examples of known prior art are:
U.S. Pat. No. 3,657,812 which discloses a retractable tool holder;
S. Pat. No. 5,071,426 which discloses a surgical scalpel with a retractable blade guard;
U.S. Pat. No. 5,116,351 which discloses a safety scalpel having a blade protecting sheath;
U.S. Pat. No. 5,139,507 which discloses a surgical scalpel with a retractable blade guard; and
U.S. Pat. No. 5,141,517 which discloses a retractable instrument automatically actuating the instrument to extend forward from a protective sheath.

The present invention solves many of the problems associated with prior art scalpels and latch mechanisms.

SUMMARY OF THE INVENTION

The present invention provides a tool holder in which a tool retracts into a chassis of the tool holder when not in use such that the tool is shielded.

In one embodiment, it is specifically intended that this tool be a scalpel which functions much like a typical retractable ball point pen with its simple actuation and detent type of release.

One advantage of one embodiment of the present invention is to provide a scalpel having a retractable blade which is relatively inexpensive to produce.

One advantage of the present invention is to provide a scalpel that is free of encumbrance long the entire length of the blade in its extended operative position.

In one embodiment of the present invention, there is provided a scalpel, in either an extended or a retracted position, which has no element or part, such as a pin, screw, fastener, link, or spring, that could become dislodged and be lost in a patient's tissues or body cavity.

In one embodiment of the present invention, the retractable scalpel comprises a tubular sheath member and a tubular blade support member which are secured together by a locking collar.

In one embodiment, the blade support member is slidably mounted and partially disposed in the sheath member. A cutting blade, connectible to one end of the blade support member, is shielded in the sheath member when the scalpel is not in use. The blade is extended from the sheath member and exposed when the scalpel is in its operative position.

Still in one embodiment, when the scalpel is in its operative position, the blade support member is forced forward against the strain of a spring and is locked by a latch mechanism. The blade support member is automatically released by deactuating the latch mechanism when the scalpel is not in use. Accordingly, when the blade support member is forced forward, the cutting blade extends from the sheath member. When the blade support member is released backward, the cutting blade retracts into the sheath member.

Further in one embodiment, a first spring is disposed between a back end of the blade support member and proximate the back end of the sheath member. The spring is compressed in the operative position.

In one embodiment, the blade support member comprises a pair of transversely elongated and longitudinally extended slots wherein one of the slots is disposed at a top side and another slot is disposed at a bottom side of the blade support member. When the scalpel is made into its operating position, the latch mechanism is longitudinally slid along the slots, and is received in an enlarged slot portion disposed proximate a back end of the top side slot.

Still in this embodiment, the latch mechanism includes an upper section, an enlarged section integrated with the upper section, and a lower section. A second spring is compressed under the upper section when the scalpel is not in use. The enlarged section is received into the enlarged slot portion by sliding and pushing the blade support member toward a front end of the blade support member. Upon the receipt of the latch mechanism enlarged section into the enlarged slot portion, the first spring is compressed and the already compressed second spring extends so as to force the enlarged section into the enlarged slot portion so as to lock the blade support member in place.

Still in this embodiment, the latch mechanism is deactuated by transversely compressing the second spring to separate the enlarged section from the enlarged slot portion. The first spring extends backward so as to retract the blade into the sheath member wherein the scalpel is not in use. The latch mechanism serves an additional function in that it prevents the scalpel from rolling more than 180° on a surface.

Furthermore, in one embodiment, a limiting pin and a stop pin are disposed on each side of the latch mechanism which are used to limit the blade extending movement of the blade support member and to stop the blade retracting movement of the blade support member, respectively.

In one embodiment, the blade is removably and securely attached into the blade support member by a blade receiving portion and a fitting member.

In one embodiment, the scalpel is made of stainless steel or any disposable plastic material.

Yet in one embodiment, a plurality of holes are disposed on top and bottom sides of the sheath member so that it reduces the weight of the scalpel, as well as easily washes away blood products from the blade during non-use.

Further in one embodiment, the front end of the sheath member is beveled.

Yet in one embodiment, an external surface of the sheath member is knurled so that the operator can easily control the scalpel during the operation.

BRIEF DESCRIPTION OF THE DRAWINGS

In the drawing in which like reference numerals and letters generally indicate corresponding parts throughout the several views.

FIG. 3 is a longitudinal cross-sectional view of the scalpel shown in FIG. 1 when the scalpel is in an inoperative position.

FIG. 4 is a longitudinal cross-sectional view of the scalpel shown in FIG. 1 when the scalpel is in an operative position.

DETAILED DESCRIPTION OF THE PREFERRED EMBODIMENT

Figure 1:
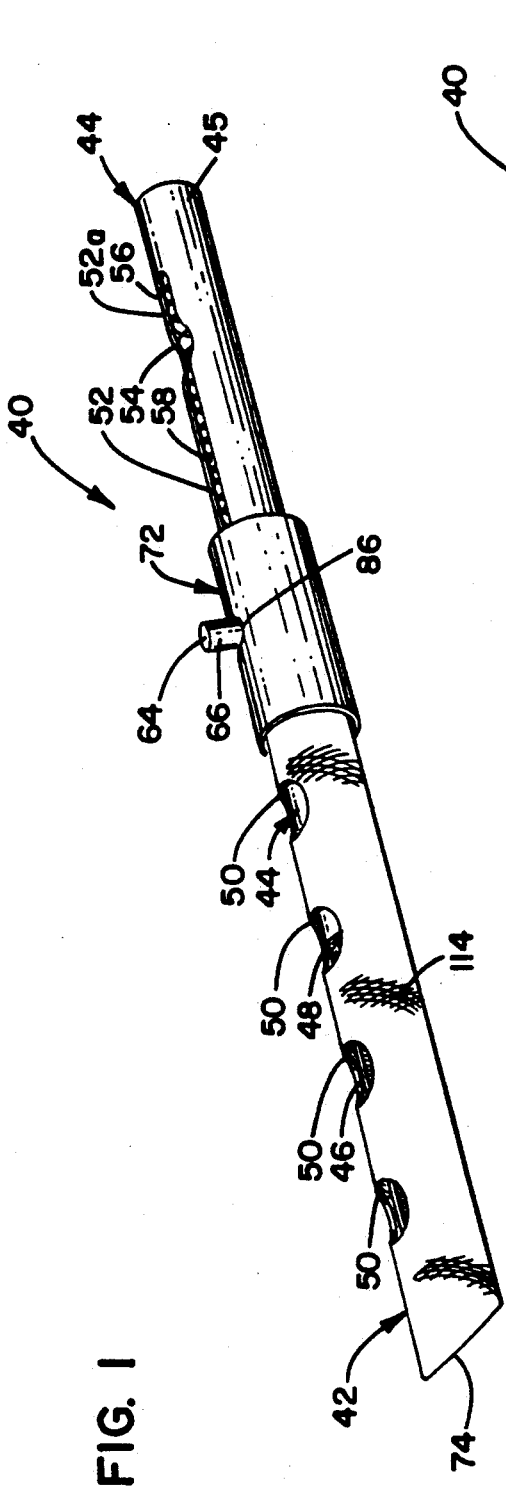
FIG. 1 is a perspective view of an embodiment of a retractable scalpel in accordance with the principles of the present invention when the scalpel is in an inoperative retracted position.

Referring to the Figures, there is shown an embodiment of a retractable scalpel, designated 40, generally in accordance with the principles of the present invention.

The scalpel 40 broadly comprises a tubular barrel or sheath member 42 and a blade support assembly 44 including an inner tubular blade support member 45 which is received telescopically within the sheath member 42. A surgical blade 46, which is mounted on a front end 48 of the blade support assembly 44, is shielded in the sheath member 42. A plurality of holes 50 are disposed on a top side and a bottom side (not shown) of the sheath member 42. The surgical blade 46 is in communication with outside through the holes 50. Accordingly, the holes reduce the weight of the scalpel 40 as well as facillitatively washing away blood products from the blade 46.

The blade support member 45 includes a pair of longitudinally extended, diametrically opposed slots 52,53 wherein the slot 52 is disposed at a top side of the blade support member 45 and the slot 53 is disposed at a bottom side (shown in FIGS. 3, 4) of the blade support member 45. An enlarged slot portion 54 is disposed proximate a back end 56 of the top side slot 52, a portion of the slot 52, shown as a slot portion 52a in FIGS. 3 and 4, extending beyond the enlarged slot portion 54. The slot 53 also extends beyond the enlarged slot portion 54. The enlarged slot portion 54 is able to receive a larger diameter member than the other portion of the top side slot 52. Further, upon receipt of the larger diameter member, which has the diameter larger than the top side slot 52 but smaller than the enlarged slot portion 54, into the enlarged slot portion 54, the member is longitudinally locked relative to the sheath member 42 and the blade support member 45.

A spring 58, which is received between a diameter reducing end cap 60 (see FIG. 3) of the blade support member 45 and a limiting pin 61 at the back end 62 of the sheath member 42, is visible from outside through the slots 52, 53. The spring 58 is compressed or released between the limiting pin 61 and the end cap 60 when the blade support assembly 44 is slidably moved relative to the sheath member 42.

A latch mechanism 64 is disposed proximate the back end 62 of the sheath member 42. The latch mechanism 64 includes a push button section 66, a spring 76 and a bottom section 65 which comprises a bottom pin section 67, a flange section 69 and a hollow section 71. The push button section 66 transversely projects from the top side slot 52 and a top opening 68 of the sheath member 42, while the bottom pin section 67 projects from the bottom side slot 53 and a bottom opening 70 in the sheath member 42 which is diametrically opposite to the top opening 68 (shown in FIG. 3). The openings 68,70 are in transverse alignment with the slots 52,53 wherein the diameter of the top opening 68 is larger than the top side slot 52 and the diameter of the bottom opening 70 is smaller than the slots 52,53.

A locking collar 72 receives the latch mechanism 64, and locks the latch mechanism 64, the sheath member 42 and the blade support assembly 44 together. The structure of the locking collar 72 will be discussed later.

Figure 2:
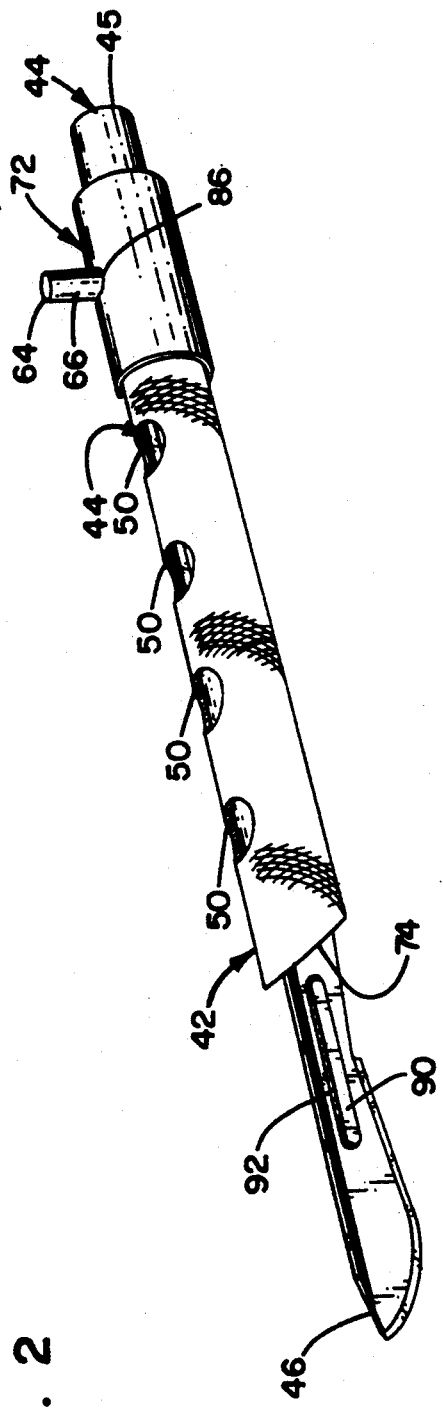
FIG. 2 is a perspective view of the scalpel shown in FIG. 1 when the scalpel is in an operative extended position.

Now referring to FIG. 2, the blade 46 is shown extending from the sheath member 42 in the operative position. The blade support assembly 44 is pushed toward a front end 74 of the sheath member 42 and the spring 58 is compressed accordingly. The front end 74 of the sheath member 42 is beveled. Thus, the whole portion of the blade 46 which contacts a cutting piece (not shown) is wholly exposed so that the surgeon can have a larger view of the cutting piece.

FIGS. 3 and 4 show longitudinal cross-sectional views of FIGS. 1 and 2 respectively, wherein the blade 46 is shielded under the sheath member 42 in FIG. 3 when the scalpel is in the retracted, inoperative position, while the blade 46 is projected from the sheath member 42 in FIG. 4 when the scalpel 40 is in the extended, operative position.

In FIG. 3, the spring 76 is compressedly disposed under the push button section 66 and received in the hollow section 71 of the latch mechanism 46. An enlarged section 78 of the push button section 66, has a larger diameter than the top side slot 52 but smaller than the diameter of the enlarged slot portion 54. Thus, the enlarged section 78 is disposed underneath the top side slot 52 as well as the top opening 68 of the sheath member 42. Accordingly, the spring 76 is kept compressed between the push button section 66 and the bottom section 65 when the scalpel 40 is not in use. As mentioned above, the push button section 66 projects through the top side slot 52 and the top opening 68 of the sheath member 42, while the bottom pin section 67 projects from the bottom side slot 53 and the bottom opening 70 of the sheath member 42.

Now referring to FIG. 4, there is shown a cross-sectional view of the scalpel 40 having the blade extended from the sheath member 42. The blade support assembly 44 is slidably moved toward the front end 74 of the sheath member 42 during which the enlarged section 78 is able to align with the enlarged slot portion 54. When the enlarged section 78 aligns with the enlarged slot portion 54, the enlarged section 78 is automatically received into the enlarged slot portion 54 of the blade support member 45 as well as the top opening 68 as a result of the spring 76 extending. Thereupon, the latch mechanism 64 stops the longitudinal movement between the sheath member 42 and the blade support assembly 44.

The latch mechanism 64 is disposed between the limiting pin 61 and a stop pin 80. The stop pin 80 is aligned with the slots 52,53. The stop pin 80 engages a front end 49 of the slots 52, 53. Thus, the stop pin 80 reduces the possibility of damages of the latch mechanism 64. Upon pushing the push button section 66, the enlarged section 78 is accordingly pushed away from the enlarged slot portion 54 so as to allow the longitudinal movement between the sheath member 42 and the blade support assembly 44. Therefore, the blade support assembly 44 is automatically released backward so as to retract the blade into the sheath member 42.

Figure 5:
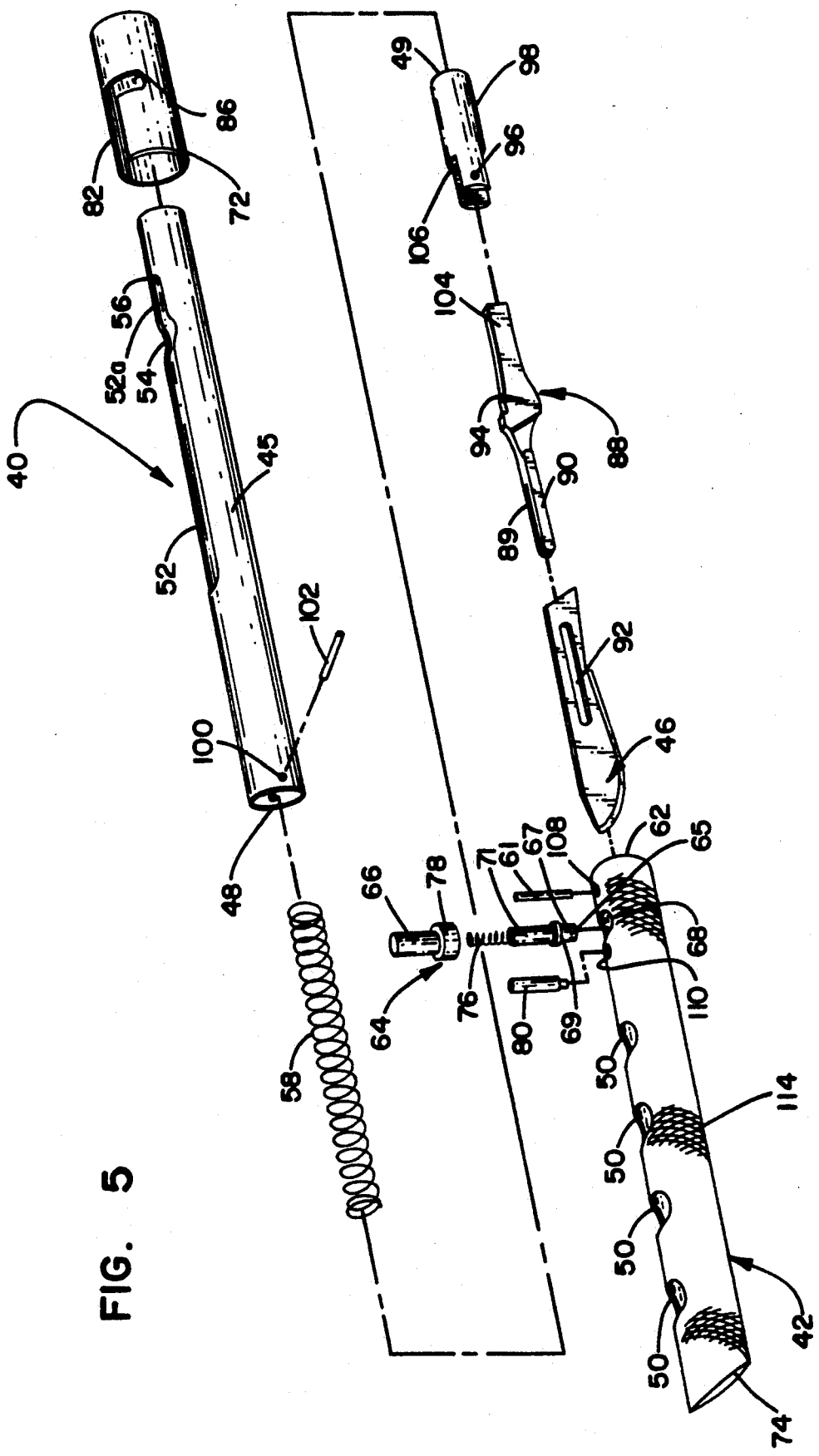
FIG. 5 is an exploded assembly view of the scalpel shown in FIG. 1.

Now referring to FIG. 5, an exploded view of scalpel 40 is shown. The locking collar 72 includes a L-shape slot 82 on a top side of the locking collar 72, and an opening 84 (shown in FIGS. 3, 4) on a bottom side of the locking collar 72. The push button section 66 is received in a slot terminal point 86 which is disposed at one end of the L-shape slot 82. The bottom pin section 67 projects outside through the bottom opening 84. The diameter of the opening 84 is smaller than that of the slot terminal point 86 so that the opening 84 receives a smaller size of the bottom pin section 67, while the slot terminal point 86 receives a larger size of the push button section 66. Consequently, the L-shape slot 82 secures the sheath member 42, the blade support assembly 44 and the latch mechanism 64 together. Further, the slot terminal point 86 is smaller than the diameter of the enlarged section 78 of the latch mechanism 64. Thus, the locking collar 72 retains the latch mechanism 64 in place on the scalpel 40.

Now referring to the blade 46 and its mounting mechanism. A blade receiving portion 88, having a needle-like head 89, includes a longitudinal projection 90 which is received into a corresponding slot 92 on the blade 46. A through hole 94 which is disposed on the blade receiving portion 88 aligns with a corresponding through hole 96 on a fitting portion 98 and further aligns with a corresponding through hole 100 on the blade support member 45. A pin 102, having a length the same as the diameter of the blade support member 45, passes through the through holes 94,96 and 100 so as to secure the blade 46 onto the blade support member 45. The blade receiving portion 88 can be replaced by removing the pin 102. A back portion 104 of the blade receiving portion 88 is received in a bore 106 of the fitting portion 98. The blade receiving portion 88 and the fitting portion 98 are standard and universal which are able to receive most regular scalpel blades. It will be appreciated that various blade mounting detach mechanisms might be used.

The limiting pin 61, having a length the same as the diameter of the sheath member 42, passes through a pair of transversely opposite openings 108 in the sheath member 42 and extends into the slot portion 52a and the slot 53. The stop pin 80, having a length the same as the diameter of the sheath member 42, passes through a top opening 110 and a transversely opposite bottom opening 112 in the sheath member 42. The stop pin 80 has a top portion larger than a bottom portion which are respectively received in the larger top opening 110 and the smaller bottom opening 112.

The scalpel 40 is made of stainless steal in the preferred embodiment. Alternatively, the scalpel 40 can be made of any kind of metal or plastic materials.

Further, an external surface 114 of the sheath member 42 is knurled so that the surgeon can easily grab or control the scalpel 40 during the operation.

When the scalpel 40 is in use, the blade support assembly 44 is pushed forward. The blade 46 is exposed outside of the sheath member 42 accordingly. The scalpel 40 is locked into an operative position when the enlarged section 78 engages with the enlarged slot portion 54.

When the scalpel 40 is not in use, the push button section 66 is pushed transversely. The blade support assembly 44 is automatically retracted and the blade 46 is accordingly shielded in the sheath member 42.

In assembling the scalpel 40, the longitudinal projection of the blade receiving portion 88 is received in the slot 92 of the blade 46. The blade receiving portion 88 is placed into the bore 106 of the fitting portion 98. The spring 58 is inserted and disposed at the end cap 60. The blade 46, the blade receiving portion 88 and the fitting portion 98 are inserted into the front end 48 of the blade support member 45. The through holes 94, 96 and 100 are aligned to each other and receive the pin 102 therebetween. Thus, the blade assembly 44 is formed.

The blade support assembly 44 is then slidably inserted into the sheath member 42 until the slots 52, 53 align with the openings 68, 70, respectively. The pins 61, 80 are inserted into the openings 108 and 110,112, respectively. The bottom section 65, the spring 76 and the push button section 66 are inserted in the slots 52,53 and the enlarged slot portion 54 from the top opening 68 to the bottom opening 70. The bottom pin section 67 is received in the bottom opening 70 while the flange section 69 stops the further insertion of the bottom pin section 67. The spring 76 is positioned in the hollow section 71 between the bottom pin section 67 and the push button section 66. At this moment, the enlarged section 78 is disposed outside of the top side slot 52. The blade support assembly 44 is pushed to allow the enlarged section 78 aligning with the enlarged slot portion 54 so that the enlarged section 78 is able to move underneath the top side slot 52. The bottom pin section 67 is pushed into the bottom side slot 53 to allow the locking collar 72 to slide over the latch mechanism 64. The locking collar 72 is slid over the back end of 62 the sheath member 42. The locking collar 72 is moved along the L-shaped slot 82 to the position where a clockwise rotation of the locking collar 72 is allowed. Then the locking collar 72 is rotated in a clockwise manner to allow the latch mechanism 64 slide into the slot terminal point 86. The push button section 66 is received in the slot terminal point 86, while the bottom pin section 67 projects through the bottom side slot 53, the bottom opening 70 of the sheath member 42 and the bottom opening 84 of the locking collar 72. Upon this step, the scalpel 40 is assembled.

The scalpel 40 can be disassembled following the reverse procedures of assembling the scalpel 40.

The blade 46 can be replaced by any type of standard scalpel blade. In replacing the blade 46, the blade 46 is simply removed from the longitudinal projection 90 of the blade receiving portion 88.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A retractable scalpel, comprising:
a sheath member having front and back ends;
a blade support member partially disposed in the sheath member and telescopically received in the sheath member for movement between an inoperative position wherein the blade support member is retracted into the sheath member, and an operative position wherein the blade support member extends out of the sheath member;
said blade support member having a pair of transversely elongated and longitudinally extended slots wherein one of the slots is disposed along a top side of the blade support member and the other slot is disposed along a bottom side of the blade support member, an enlarged slot portion disposed proximate a back end of the top side slot, a first spring member being disposed inside of the blade support member;
said sheath member including a pair of diametrically opposite top and bottom openings in transverse alignment with said slots;
latch means, having a push button section projecting through said top opening and said top side slot, and a bottom section projecting through said bottom opening and said bottom side slot, for latching the scalpel in an extended, operative position, the push button section being telescopically received by the bottom section, an enlarged section being disposed on said push button section for receipt in the enlarged slot portion upon alignment therewith, thereby locking the sheath member and the blade support member against further relative movement, a second spring member being disposed between the push button section and the bottom section of the latch means;
locking collar means for securing the blade support member, the sheath member and the latch means together;
means for mounting a blade on the blade support member; and
means for limiting movement of the blade support member beyond the operative position and the inoperative position including means for transversely extending through the top side and bottom side slots of said blade support member and a pair of oppositely disposed openings of the sheath member which are in alignment with the top side and bottom side slots of said blade support member.

2. A retractable tool holder, comprising:
a sheath member having front and back ends;
a tool support member partially disposed in the sheath member;
means for mounting a tool on the tool support member;
the tool support member being telescopically received in the sheath member for movement between an inoperative position wherein the tool is retracted into the sheath member, and an operative position wherein the tool extends out of the sheath member;
said tool support member having a pair of transversely elongated and longitudinally extended slots wherein one of the slots is disposed along a top side of the blade support member and the other slot is disposed along a bottom side of the blade support member, an enlarged slot portion disposed proximate a back end of one of the extended slots, a spring being disposed inside of the tool support member;
latch means for latching the scalpel in an extended, operative position, the latch means having an enlarged section being receivable in the enlarged slot portion upon alignment therewith, thereby locking the sheath member and the tool support member against further relative movement;
locking collar means for securing the tool support member, the sheath member and the latch means together; and
means for limiting movement of the tool support member beyond the operative position and inoperative position including means for transversely extending through the top and bottom lots of the tool support member.

3. A retractable scalpel, comprising:
a sheath member having front and back ends;
a blade support member partially disposed in the sheath member and telescopically received in the sheath member for movement between an inoperative position wherein the blade support member is retracted into the sheath member, and an operative position wherein the blade support member extends out of the sheath member;
said blade support member having a pair of transversely elongated and longitudinally extended slots wherein one of the slots is disposed along a top side of the blade support member and the other slot is disposed along a bottom side of the blade support member, an enlarged slot portion disposed proximate aback end of the top side slot, a first spring member being disposed inside of the blade support member;
said sheath member including a pair of diametrically opposite top and bottom openings in transverse alignment with said slots;
latch means, having a push button section projecting through said top opening and said top side slot, and a bottom section projecting through said bottom opening and said bottom side slot, for latching the scalpel in an extended, operative position, the push button section being telescopically received by the bottom section, an enlarged section being disposed on said push button section for receipt in the enlarged slot portion upon alignment therewith, thereby locking the sheath member and the blade support member against further relative movement, a second spring member being disposed between the push button section and the bottom section of the latch means;

locking collar means for securing the blade support member, the sheath member and the latch means together; and means for mounting a blade on the blade support member.

4. A retractable scalpel in accordance with claim 1, wherein the diameter of the top opening of the sheath member is larger than the slots and a diameter of the bottom opening of the sheath member is the same as the slots.

5. A retractable scalpel in accordance with claim 4, further comprising means for limiting movement of the blade support member beyond the operative position.

6. A retractable scalpel in accordance with claim 5, further comprising means for stopping movement of the blade support member beyond the inoperative position.

7. A retractable scalpel in accordance with claim 6, wherein the limiting means includes a pin transversely extending through the top side and bottom side slots of said blade support member and a pair of oppositely disposed openings of the sheath member which are in alignment with the top side and bottom side slots of said blade support member.

8. A retractable scalpel in accordance with claim 7, wherein the stopping means includes a pin transversely extending through the top side and bottom side slots of said blade support member and a pair of oppositely disposed openings of the sheath member which are in alignment with the top side and bottom side slots of the blade support member.

9. A retractable scalpel in accordance with claim 8, wherein the locking collar means includes a locking collar having a L-shape slot and a collar pin opening, a bottom pin section of the bottom portion of the latch means is received in the collar pin opening, the push button section of the latch means is received in a slot terminal portion of the L-shape slot.

10. A retractable scalpel in accordance with claim 9, wherein the mounting means includes a blade receiving portion and a fitting portion, the blade having a slot receiving a projection on a needle head of the blade receiving portion, a through hole being disposed on the blade receiving portion, the blade receiving portion being received in the fitting portion, a corresponding through hole of the fitting portion aligning with said through hole of the blade receiving portion and further aligning with a through hole disposed at the front end of the blade support member, a locking pin extending through said through holes so as to secure the blade on the blade support member.

11. A retractable scalpel in accordance with claim 10, wherein the scalpel is made of stainless steel.

12. A retractable scalpel in accordance with claim 11, wherein the scalpel is made of metal.

13. A retractable scalpel in accordance with claim 12, wherein the scalpel is made of plastic material.

14. A retractable scalpel in accordance with claim 13, a plurality of holes disposed on top and bottom sides of the sheath member.

15. A retractable scalpel in accordance with claim 14, wherein the back end portion of the blade support member includes a diameter reducing end cap which receives the first spring member therein.

16. A retractable scalpel in accordance with claim 15, wherein the front end of the sheath member is beveled.

17. A retractable scalpel in accordance with claim 16, wherein an external surface of the sheath member is knurled.

18. A retractable tool holder, comprising:
a sheath member having front and back ends;
a tool support member partially disposed in the sheath member;
means for mounting a tool on the tool support member;
the tool support member being telescopically received in the sheath member for movement between an inoperative position wherein the tool is retracted into the sheath member, and an operative position wherein the tool extends out of the sheath member;
said tool support member having at least one transversely elongated and longitudinally extended slot, an enlarged slot portion disposed proximate a back end of the slot, a spring being disposed inside of the tool support member, the sheath member having spring engaging means for engaging a front end of the spring so that the spring is compressed upon movement of the tool support member into the sheath member;
latch means for latching the scalpel in an extended, operative position, the latch means having an enlarged section being receivable in the enlarged slot portion upon alignment therewith, thereby locking the sheath member and the tool support member against further relative movement;
locking collar means for securing the tool support member, the sheath member and the latch means together; and
limiting means in back of the enlarged slot portion for limiting movement beyond a predetermined position of the tool support member into the sheath member.

19. A retractable tool holder in accordance with claim 18, wherein the limiting means extends into the slot of the tool support member so as to engage an end of the slot upon movement of the tool support member into the operative position.

20. A retractable tool holder in accordance with claim 18, including stop means in front of the enlarged slot portion for stopping movement beyond a predetermined position of the tool support member, wherein the stop means extends into the slot of the tool support member so as to engage the other end of the slot upon movement of the tool support member out of the operative position.

* * * * *